(12) United States Patent
Mishkhes et al.

(10) Patent No.: US 10,481,292 B2
(45) Date of Patent: *Nov. 19, 2019

(54) STATISTICAL METHODS FOR ASSESSING DOWNHOLE CASING INTEGRITY AND PREDICTING CASING LEAKS

(71) Applicant: Saudi Arabian Oil Company, Dhahran (SA)

(72) Inventors: Abdulrahman Mishkhes, Dhahran (SA); Mohammed D. Al-Ajmi, AlKhobar (SA); Mubarak J. Al-Shammari, AlKhobar (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

This patent is subject to a terminal disclaimer.

(21) Appl. No.: 16/119,717

(22) Filed: Aug. 31, 2018

(65) Prior Publication Data

US 2019/0064385 A1 Feb. 28, 2019

Related U.S. Application Data

(63) Continuation of application No. 14/795,183, filed on Jul. 9, 2015, now Pat. No. 10,107,932.

(51) Int. Cl.
*G01V 3/38* (2006.01)
*E21B 47/00* (2012.01)
(Continued)

(52) U.S. Cl.
CPC .............. *G01V 3/38* (2013.01); *E21B 47/00* (2013.01); *G01N 17/04* (2013.01); *G01V 3/18* (2013.01)

(58) Field of Classification Search
CPC .............. G01V 3/38; G01V 3/18; G01N 17/04
See application file for complete search history.

(56) References Cited

U.S. PATENT DOCUMENTS 7,107,154 B2 9/2006 Ward
7,346,455 B2 3/2008 Ward et al.
(Continued)

OTHER PUBLICATIONS

Gulf Cooperation Council Examination Report issued in GCC Application No. 2016-31165 dated Oct. 12, 2018, 4 pages.
(Continued)

*Primary Examiner* — Anthony Ho
(74) *Attorney, Agent, or Firm* — Fish & Richardson P.C.

(57) ABSTRACT

The present disclosure describes methods and systems, including computer-implemented methods, computer program products, and computer systems, for predicting casing leaks. One computer-implemented method includes obtaining raw electromagnetic (EM) corrosion data for a hotspot, wherein the raw EM corrosion data includes a metal thickness loss value for the hotspot; determining a corrosion parameter based on the raw EM corrosion data; generating a probability distribution curve for the corrosion parameter; generating a corrosion severity classification matrix based on the probability distribution curve, wherein the corrosion severity classification matrix includes a plurality of corrosion severity classes and cutoff values for each of the plurality of corrosion severity classes; and assigning the hotspot into one of the plurality of corrosion severity classes based on the corrosion severity classification matrix and the corrosion parameter of the hotspot.

6 Claims, 7 Drawing Sheets

(51) Int. Cl.
  *G01N 17/04* (2006.01)
  *G01V 3/18* (2006.01)

(56) References Cited

U.S. PATENT DOCUMENTS

| | | | |
|---|---|---|---|
| 7,526,944 | B2 | 5/2009 | Sabata et al. |
| 7,711,486 | B2 | 5/2010 | Thigpen et al. |
| 8,041,517 | B2 | 10/2011 | Thayer et al. |
| 10,107,932 | B2 * | 10/2018 | Mishkhes ............... E21B 47/00 |
| 2001/0037675 | A1 | 11/2001 | Kuo |
| 2007/0256942 | A1 | 11/2007 | Atherton |
| 2010/0300184 | A1 | 12/2010 | Wayman et al. |
| 2012/0136577 | A1 | 5/2012 | Dria et al. |
| 2013/0087328 | A1 | 4/2013 | Maida, Jr. et al. |
| 2013/0304680 | A1 | 11/2013 | Bailey et al. |
| 2014/0214326 | A1 | 7/2014 | Samuel et al. |

OTHER PUBLICATIONS

AlAjmi, Mohammed et al.; "Profiling Downhole Casing Integrity Using Artificial Intelligence"; Society of Petroleum Engineers; SPE Digital Energy Conference and Exhibition; The Woodlands, Texas; Mar. 5, 2015; pp. 1-13.

Al-Janabi, Yahya T. et al.; "Monitoring of Downhole Corrosion: An Overview"; Society of Petroleum Engineers; Annual Technical Symposium and Exhibition; Khobar, Saudi Arabia; May 22, 2013; pp. 1-11.

Brill et al., "Electromagnetic Casing Inspection Tool for Corrosion Evaluation", IPTC 14865, Copyright 2011, 14 pages.

Garcia, Javier et al.; "Successful Application of a New Electromagnetic Corrosion Tool for Well Integrity Evaluation in Old Wells Completed with Reduced Diameter Tubular"; Society of Petroleum Engineers; International Petroleum Technology Conference; Beijing, China; Mar. 28, 2013; pp. 1-12.

Wheeler et al., "Improving Field Economics Through the Use of Modern Casing-Corrosion Logging Tools and Techniques," SPE 49297, Copyright 1998, 16 pages.

International Search Report and Written Opinion of the International Searching Authority issued in International Application No. PCT/US2015/059149 dated May 17, 2016; 14 pages.

Gulf Cooperation Council Examination Report issued in GCC Application No. 2016-31165 dated May 31, 2018, 4 pages.

* cited by examiner

Corrosion Severity Classification Definition Table

| Corrosion Class | Average Metal Loss % | | ARB | | Corrosion Rate | | Expected Life | |
|---|---|---|---|---|---|---|---|---|
| | From | To | From | To | From | To | | |
| 3 | $<X_{ML2}$ | | $>X_{ARB2}$ | | $<X_{CR2}$ | | $<X_{EL2}$ | |
| 2 | $X_{ML2} = X_{ML1} - \alpha_{NLML}$ | $X_{ML1}$ | $X_{ARB2} = X_{ARB1} + \alpha_{NLARB}$ | $X_{ARB1}$ | $X_{CR2} = \mu_{NLCR}$ | $X_{CR1}$ | $X_{EL2} = \mu_{NLEL}$ | $X_{EL1}$ |
| 1 | $X_{ML1} = X_{ML0} - \alpha_{LML}$ | $X_{ML0}$ | $X_{ARB1} = X_{ARB0} + \alpha_{LARB}$ | $X_{ARB0}$ | $>=X_{CR1}$ $X_{CR1} = \mu_{NLCR} + \alpha_{NLCR}$ | | $<=X_{EL1}$ $X_{EL1} = \mu_{NLEL} - \alpha_{NLEL}$ | |
| 0 | $>=X_{ML0}$ $X_{ML0}$= the larger of $\mu_{LML} - \alpha_{LML}$ or $\mu_{NLML} + \alpha_{NLML}$ | | $<=X_{ARB0}$ $X_{ARB0}$= the smaller of $\mu_{LARB} + \alpha_{LARB}$ or $\mu_{NLARB} - \alpha_{NLARB}$ | | | | | |

FIG. 5A — 510

Corrosion Severity Classification Matrix

| Expected Life (years) | Average Metal Loss % | Corrosion Rate (mpy) | Average Number of Remaining Barriers/Strings | Corrosion Class | Indicative Inspection Frequency (years) |
|---|---|---|---|---|---|
| More than 33 | 0 to 24% | 0 to 5.85 | More than 2.30 | 3 | 8 years |
| 10 to 33 | 25 to 36% | 5.86 to 9.80 | 1.91 to 2.30 | 2 | 4 years |
| 1 to 9 | 37 to 48% | 9.81 to 13.70 | 1.52 to 1.92 | 1 | 2 year |
| ---- | More than 48% | More than 13.70 | Less than 1.52 | 0 | High risk to develop a leak |

FIG. 5B — 520

STATISTICAL METHODS FOR ASSESSING DOWNHOLE CASING INTEGRITY AND PREDICTING CASING LEAKS

CROSS-REFERENCE TO RELATED APPLICATIONS

This application is a Continuation Application of and claims the benefit of priority to U.S. patent application Ser. No. 14/795,183, filed on Jul. 9, 2015, the contents of which are hereby incorporated by reference.

BACKGROUND

In the petroleum industry, a service company can monitor corrosion process and/or progress of downhole drilling pipe casing hotspots (areas likely to develop casing damage due to thermal and related effects on a casing) and develop log and casing repair schedules accordingly. In some cases, the service company can use electromagnetic (EM) corrosion logging tools to collect raw EM corrosion data associated with casing hotspots to monitor the corrosion process and to provide an assessment of the integrity of multiple casings. However, EM tools only provide circumferential average readings of metal thickness loss across multiple strings rather than directional ones. Consequently, wells with casing failures show average metal loss values less than 100% unless the failure occurs around the 360° circumference. In other words, 50% average metal loss could mean a failure if one part of the casing is completely gone and the other is intact. This wide range of possibilities and uncertainty has made it extremely challenging to both interpret and analyze EM corrosion logging data.

SUMMARY

The present disclosure describes methods and systems, including computer-implemented methods, computer program products, and computer systems, for assessing downhole casing integrity and predicting casing leaks. One computer-implemented method includes obtaining, by a data processing apparatus, raw electromagnetic (EM) corrosion data for a hotspot, wherein the raw EM corrosion data includes a metal thickness loss value for the hotspot; determining, by the data processing apparatus, a corrosion parameter based on the raw EM corrosion data, wherein the corrosion parameter includes at least one of an average remaining barrier, a corrosion rate, or an expected life; generating, by the data processing apparatus, a probability distribution curve for the corrosion parameter; generating, by the data processing apparatus, a corrosion severity classification matrix based on the probability distribution curve, wherein the corrosion severity classification matrix includes a plurality of corrosion severity classes and cutoff values for each of the plurality of corrosion severity classes; and assigning, by the data processing apparatus, the hotspot into one of the plurality of corrosion severity classes based on the corrosion severity classification matrix and the corrosion parameter of the hotspot.

Other implementations of this aspect include corresponding computer systems, apparatuses, and computer programs recorded on one or more computer storage devices, each configured to perform the actions of the methods. A system of one or more computers can be configured to perform particular operations or actions by virtue of having software, firmware, hardware, or a combination of software, firmware, or hardware installed on the system that in operation causes the system to perform the actions. One or more computer programs can be configured to perform particular operations or actions by virtue of including instructions that, when executed by data processing apparatus, cause the apparatus to perform the actions.

The foregoing and other implementations can each optionally include one or more of the following features, alone or in combination:

A first aspect, combinable with the general implementation, wherein the generation of the probability distribution curve includes determining whether the hotspot is a leaking hotspot or a non-leaking hotspot; if the hotspot is a leaking hotspot, generating a probability distribution curve for the corrosion parameter based on corrosion parameters for leaking hotspots; and if the hotspot is a non-leaking hotspot, generating a probability distribution curve for the corrosion parameter based on corrosion parameters for non-leaking hotspots.

A second aspect, combinable with any of the previous aspects, wherein the raw EM corrosion data includes metal loss values for a plurality of strings, and the corrosion parameter includes the average remaining barrier that is calculated based on a nominal thickness value for each of the plurality of strings, and a thickness loss value for each of the plurality of strings.

A third aspect, combinable with any of the previous aspects, wherein the corrosion parameter includes the corrosion rate that is calculated based on an original thickness value, a remaining thickness value, and a number of years.

A fourth aspect, combinable with any of the previous aspects, wherein the generation of the probability distribution curve for the corrosion parameter includes calculating a mean value and a standard deviation value of the corrosion parameter for leaking hotspots; calculating a mean value and a standard deviation value of the corrosion parameter for non-leaking hotspots; generating a probability distribution function of the leaking hotspots based on the mean value and the standard deviation value of the corrosion parameter for leaking hotspots; and generating a probability distribution function of the non-leaking hotspots based on the mean value and the standard deviation value of the corrosion parameter for non-leaking hotspots.

A fifth aspect, combinable with any of the previous aspects, wherein the cutoff values for each of the plurality of corrosion severity classes is determined based on a mean value of the corrosion parameter for leaking hotspots, a standard deviation value of the corrosion parameter for leaking hotspots, a mean value of the corrosion parameter for non-leaking hotspots, and a standard deviation value of the corrosion parameter for non-leaking hotspots.

A sixth aspect, combinable with any of the previous aspects, wherein each of the plurality of corrosion severity classes is associated with a logging frequency for the respective corrosion severity class.

The subject matter described in this specification can be implemented in particular implementations so as to realize one or more of the following advantages. This approach may provide service companies a robust and practical methodology to analyze raw Electromagnetic (EM) corrosion logs' data and predict casing leaks. For example, this approach includes data-driven models and dynamic decision processes that can be used to analyze raw EM corrosion data, predict downhole casing leaks, and forecast completion life. This approach converts the qualitative measurements of the raw EM corrosion data into quantitative assessment of casing failures. Moreover, the approach provides a risk-based corrosion logging frequency model for safe and practical monitoring of downhole casing integrity. Other advantages will be apparent to those of ordinary skill in the art.

The details of one or more implementations of the subject matter of this specification are set forth in the accompanying drawings and the description below. Other features, aspects, and advantages of the subject matter will become apparent from the description, the drawings, and the claims.

DESCRIPTION OF DRAWINGS

FIG. 5A illustrates an example corrosion severity classification definition table according to an implementation.

FIG. 5B illustrates an example corrosion severity classification matrix according to an implementation.

Like reference numbers and designations in the various drawings indicate like elements.

DETAILED DESCRIPTION

The following description is presented to enable any person skilled in the art to make and use the disclosed subject matter, and is provided in the context of one or more particular implementations. Various modifications to the disclosed implementations will be readily apparent to those skilled in the art, and the general principles defined herein may be applied to other implementations and applications without departing from scope of the disclosure. Thus, the present disclosure is not intended to be limited to the described and/or illustrated implementations, but is to be accorded the widest scope consistent with the principles and features disclosed herein.

This disclosure generally describes methods and systems, including computer-implemented methods, computer program products, and computer systems, for predicting downhole casing leaks. In some cases, electromagnetic (EM) corrosion logging tools can provide raw corrosion data related to a casing hotspot ("hotspot"), which is an area likely to develop casing damage due to galvanic, chemical or mechanical effects on a casing. The raw EM corrosion data may include circumferential average readings of metal thickness loss. However, these readings may not include directional data or consider the different combinations and sizes of downhole casings. These factors make interpretation and analysis of raw corrosion data produced by the EM corrosion logging tools challenging because of a wide range of corrosion scenario possibilities and resultant uncertainty. For example, wells with casing failures may have average metal loss values less than 100% unless the failure occurs around the 360 degree circumference.

Figure 1:
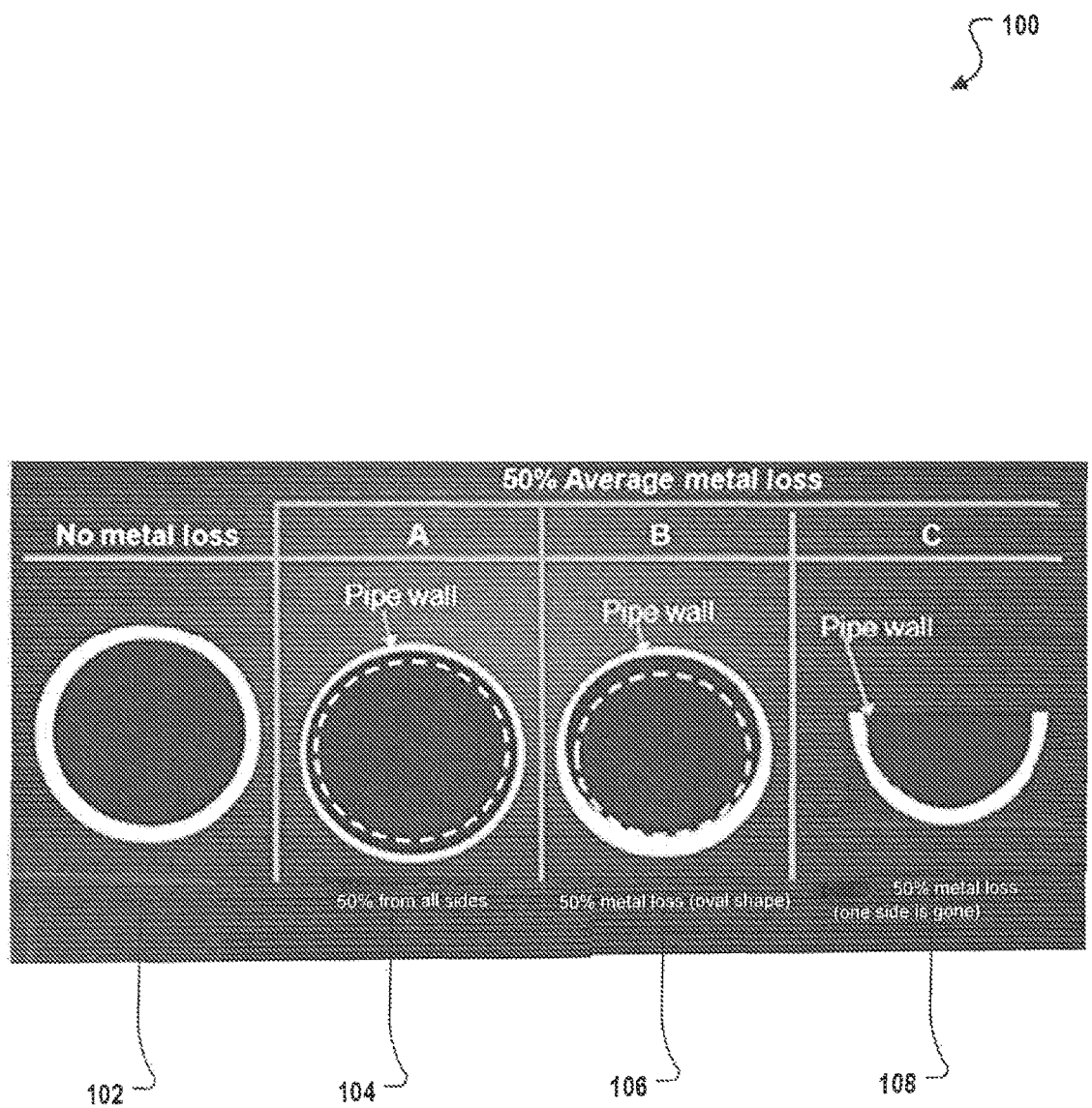
FIG. 1 is a chart illustrating example metal loss scenarios for casing hotspots according to an implementation.

FIG. 1 is a chart 100 illustrating example metal-loss scenarios for casing hotspots according to an implementation. The chart 100 includes metal-loss scenarios 102, 104, 106, and 108. In the metal-loss scenario 102, the example hotspot has no metal loss and the casing is intact. Each casing in the metal-loss scenarios 104, 106, and 108 has 50% average metal loss. In the metal-loss scenario 104, the casing has a uniform loss around the 360 degree circumference of the example casing. In the metal-loss scenario 106, the casing has a loss resulting in a cross-sectional oval shape. In the metal-loss scenario 108, the illustrated top half of the example casing has corroded away and is gone while the other side of the example casing is intact. While all three scenarios illustrate a 50% average metal loss, metal-loss scenario 108 represents a casing failure. Additionally, metal-loss scenario 104 may result in a longer expected life of the casing than the metal-loss scenario 106. Accordingly, determining whether to suspend the well from production and take the necessary remedial actions based on metal-loss scenarios is difficult.

In some cases, data-driven models and dynamic decision processes can be used to analyze electromagnetic (EM) corrosion logs, predict downhole casing leaks, and/or forecast a well completion life. Moreover, a risk-based corrosion logging frequency model can be developed to provide safe and practical monitoring of downhole casing integrity.

Figure 2:
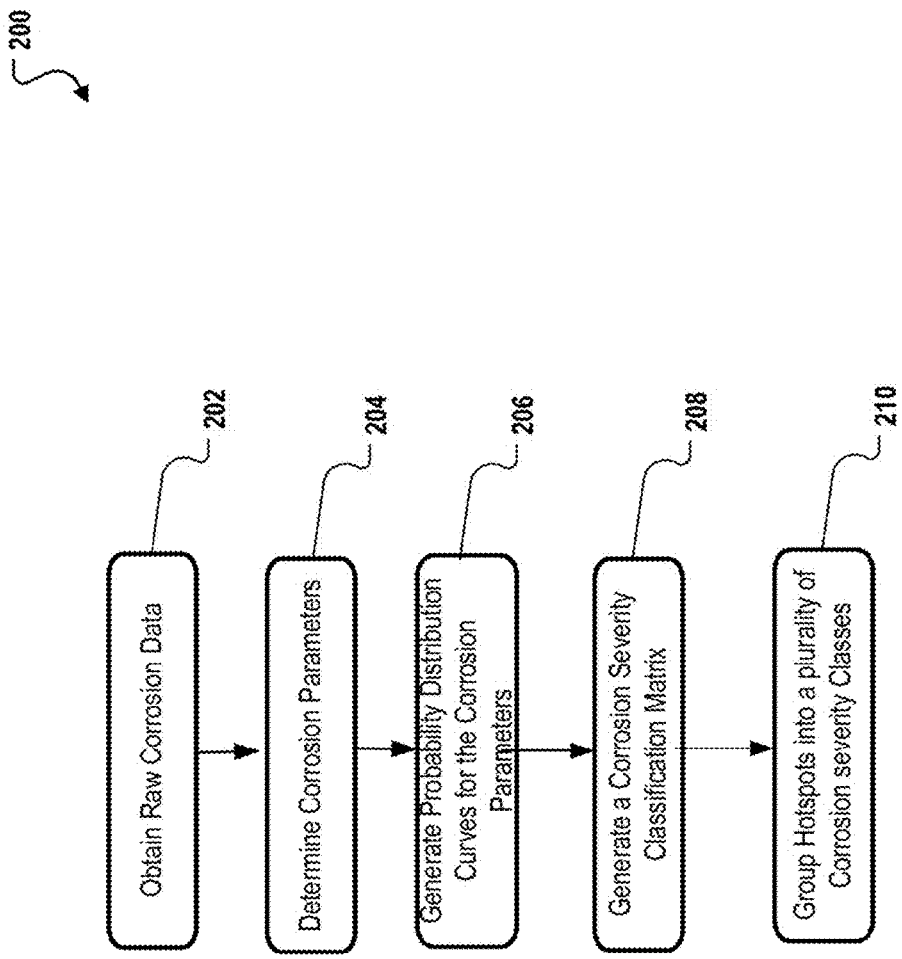
FIG. 2 illustrates an example method for predicting downhole casing leaks according to an implementation.

FIG. 2 illustrates an example method 200 for predicting downhole casing leaks according to an implementation. For clarity of presentation, the description that follows generally describes method 200 in the context of FIGS. 1, 3, 4A-4D, and 5-6. However, it should be understood by those of ordinary skill in the art that method 200 may be performed, for example, by any other suitable system, environment, software, and hardware, or a combination of systems, environments, software, and hardware as appropriate. In some implementations, various steps of method 200 can be run in parallel, in combination, in loops, and/or in any order.

At 202, raw corrosion data is obtained. In some cases, the raw corrosion data can be obtained from EM corrosion logs associated with downhole casings. For example, a user from the service company analyzing hotspots can run EM corrosion logging tools to generate corrosion logs. In some cases, raw corrosion data for more than one hotspot can be obtained from the logging tools. A casing string ("string") is a long section of connected oilfield pipe that can be lowered into a wellbore and cemented. In some cases, the corrosion logs for a hotspot can include both nominal thickness and thickness loss for one or more strings.

Figure 6:
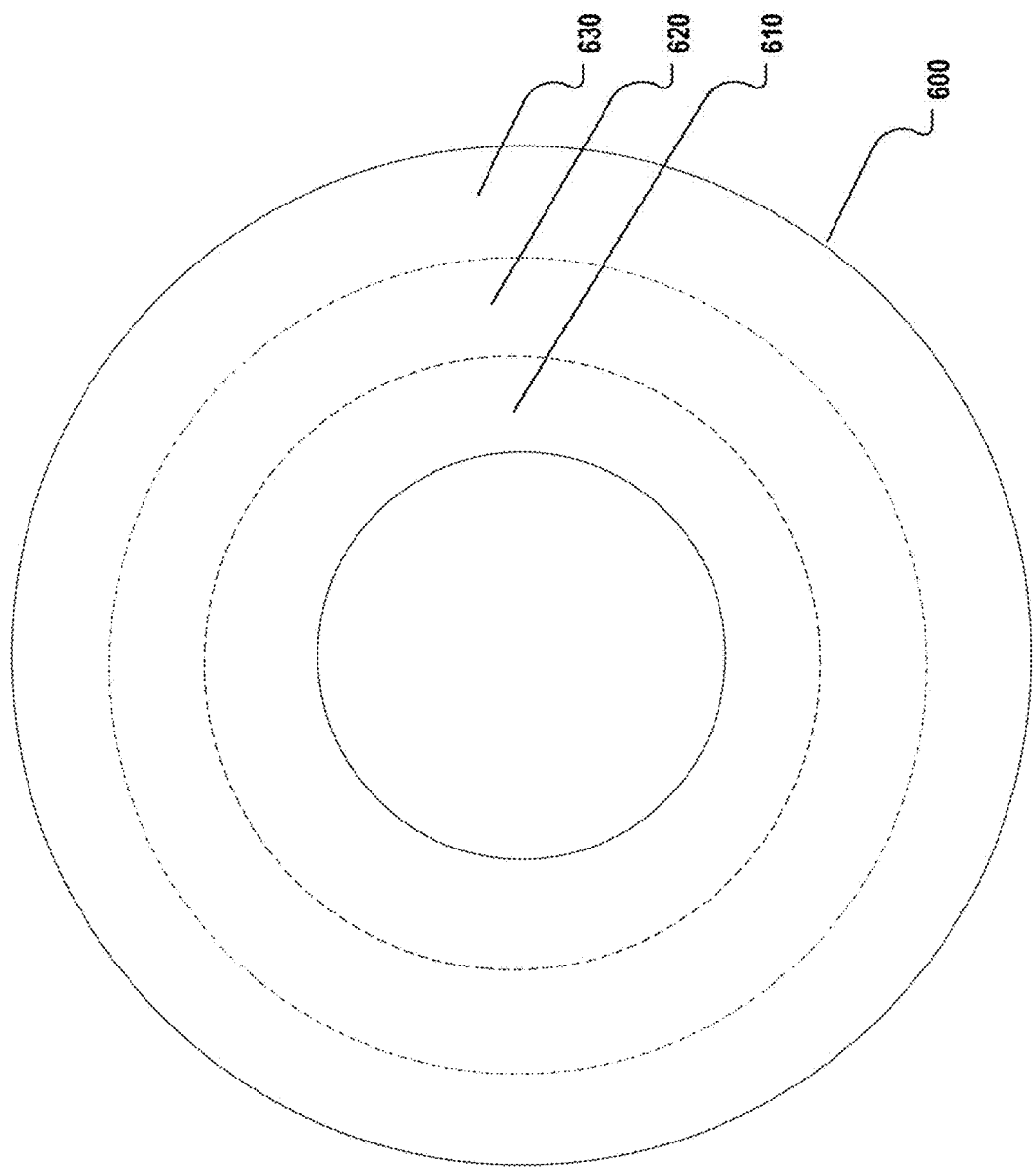
FIG. 6 illustrates a top-level view of example layered strings according to an implementation.

Turning now to FIG. 6, FIG. 6 illustrates a top-level view 600 of example layered strings according to an implementation. As shown in FIG. 6, the top-level view 600 includes a top view of strings 610, 620, and 630. In some cases, the raw corrosion data generated by EM logging tools can include a nominal thickness value for each of the strings 610, 620, and 630. The raw corrosion data can also include a metal thickness loss value for each of casing strings 610, 620, and 630.

Returning to FIG. 2, from 202, method 200 proceeds to 204.

At 204, one or more corrosion parameters for a hotspot is determined. The examples of the corrosion parameters can include an Average Remaining Barrier (ARB) value, a Corrosion Rate (CR) value, and an Expected Life (EL) value. The ARB for the hotspot is calculated based on metal thickness values for the hotspot. The ARB represents a circumferential average of a number of remaining strings between a subsurface formation, e.g., shallow water-bearing formations, and the wellbore. The ARB is a normalized parameter that accounts for different combinations and sizes of downhole casings. The following equation represents an example definition of the ARB for a hotspot:

$$ARB = X - \left[\frac{T_{L1}}{T_{N1}} + \frac{T_{L2}}{T_{N2}} + \frac{T_{L3}}{T_{N3}} \cdots \cdots \frac{T_{LX}}{T_{NX}}\right]$$

where X represents the number of strings in the hotspot, $T_{Li}$ represents the thickness loss of the i-th string, and $T_{Ni}$ represents the nominal thickness of the i-th string. From 204, method 200 proceeds to 206.

In some cases, the CR value can be calculated based on an average metal loss rate per year. For example, the CR value can be calculated based on the metal loss and a number of years since the date of a previous log. In some cases, the completion date of the hotspot can be used if the date of the last base log is not available. In some cases, the metal loss can be calculated based on the original thickness and the remaining thickness. The remaining thickness may represent the existing total average thickness of all casing strings read by the EM corrosion logging tool across the entire hotspot. The following equation represents an example definition of the CR for a hotspot in mills per year.

$$\text{Corrosion Rate(mpy)} = \frac{[\text{Original Thickness (in)} - \text{Remaining Thickness (in)}] \times 1000}{\text{Number of years since the last baselog}}$$

Alternatively or in combination, the CR can also be calculated based on average weight loss per year or rate of penetration into a casing. In some cases, CRs for leaking hotspots are not calculated because the leaking hotspots may need to be repaired before resuming service.

Based on the calculated CR, EL can be calculated based on the CR, an average remaining thickness, and a retirement thickness. In some cases, the retirement thickness can be a predefined value that represents a statistically estimated threshold below which a casing may be retired. The following equation represents an example definition of the EL:

$$\text{Expected Life(years)} = \frac{[\text{Remaining thickness (in)} - \text{Retirement thickness (in)}] \times 1000}{\text{Corrosion rate (mpy)}}$$

In some cases, ELs for leaking hotspots are not calculated because the leaking hotspots may need to be repaired before resuming service.

From 204, method 200 proceeds to 206, where the probability distribution curves for the corrosion parameters are generated. In some cases, probability distribution curves for leaking hotspots and non-leaking hotspots are generated separately. The leaking hotspots can include wells that have been confirmed to have casing failures. The non-leaking hotspots can include wells that do not have casing integrity issues. In some cases, whether a hotspot has casing failure can be determined based on a well history log or workover rig findings. In some cases, a workover may be a well intervention operation performed by a rig to maintain the wells integrity and/or productivity. In some cases, casing leaks may be confirmed by pressure testing that is conducted after pulling out the tubing and packer using a workover rig.

In some cases, the normal probability distribution curves for leaking and non-leaking hotspots can be plotted to correlate the risk of developing casing failures versus metal loss values, the ARB values, the CR values, and/or the EL values. In some cases, the metal loss values are output by the EM logging tools, while the ARB, CR, and EL values are calculated as discussed above. In addition, threshold values, beyond which the risk of developing casing leaks sharply increases, can be defined based on normal probability distribution curves. The following equations illustrate an example method of generating normal probability distribution curves based on average metal loss, ARB values, CR values, and EL values.

The mean and standard deviation of metal loss percentages of non-leaking hotspots can be determined using the following equations:

$$\mu_{NLML} = \frac{\sum_{i=1}^{n}(MLi)}{n}$$

$$\alpha_{NLML} = \sqrt{\frac{\sum_{i=1}^{n}(MLi - \mu_{NLML})^2}{n-1}}$$

where MLi represents the metal loss values in percentage of the i-th non-leaking hotspot, $\mu_{NLML}$ represents the average of the metal loss values of the non-leaking hotspot, and $\alpha_{NLML}$ represents the standard deviation of metal loss values for non-leaking hotspots.

Similarly, the mean and standard deviation of metal loss percentages of leaking hotspots can be calculated using the following equations:

$$\mu_{LML} = \frac{\sum_{i=1}^{n}(MLi)}{n}$$

$$\alpha_{LML} = \sqrt{\frac{\sum_{i=1}^{n}(MLi - \mu_{LML})^2}{n-1}}$$

where MLi represents the metal loss values in percentage of the i-th leaking hotspot, $\mu_{LML}$ represents the average of the metal loss values of the leaking hotspot, and $\alpha_{LML}$ represents the standard deviation of metal loss values for the leaking hotspots.

The metal loss probability distributions for non-leaking (P1) and leaking (P2) hotspots can be calculated in the following equations:

$$P_1(ML \geq ML_0) = \frac{1}{\sqrt{2\pi}\,\alpha_{NLML}} \int_{ML_0}^{\infty} e^{-\frac{(ML-\mu_{NLML})^2}{2\alpha_{NLMNL}^2}} dML$$

$$P_2(ML \leq ML_0) = \frac{1}{\sqrt{2\pi}\,\alpha_{LML}} \int_{-\infty}^{ML_0} e^{-\frac{(ML-\mu_{LML})^2}{2\alpha_{LML}^2}} dML$$

Figure 4A:
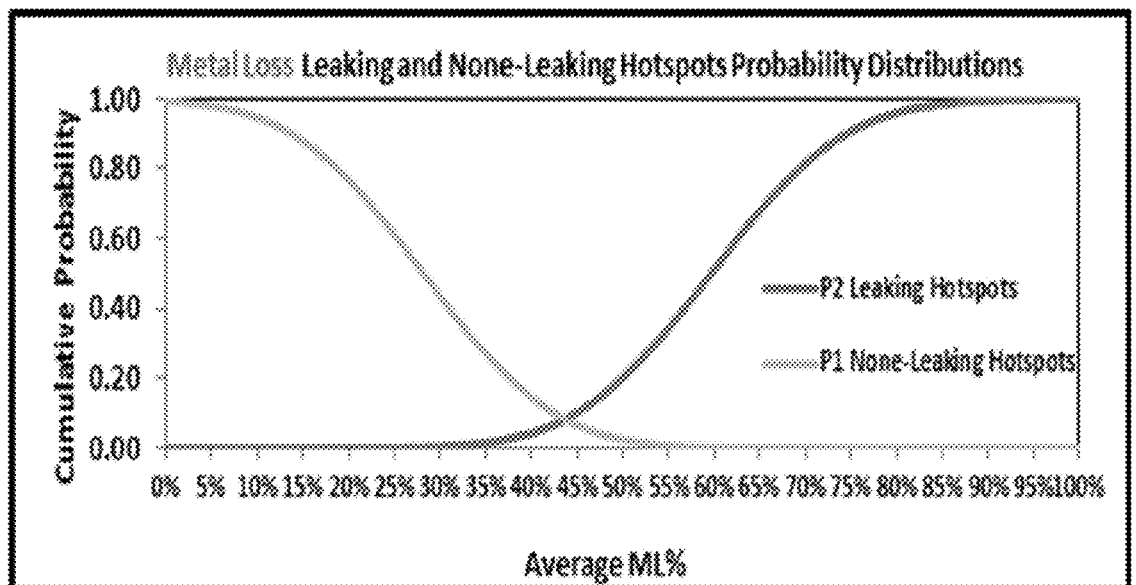
FIG. 4A is an example metal loss probability distribution chart according to an implementation.

FIG. 4A is an example metal loss probability distribution chart 410 according to an implementation. The example metal loss probability distribution chart 410 includes metal loss probability distribution curves for the leaking and non-leaking hotspots based on the above-described equations. For example, as shown in FIG. 4A, 50% of the leaking hotspots have average metal loss values of about 60% or higher, while 50% of the non-leaking hotspots have average metal loss values of about 30% or higher.

Referring to FIG. 2, the mean and standard deviation of ARB values for non-leaking hotspots can be calculated as follows:

$$\mu_{NLARB} = \frac{\sum_{i=1}^{n}(ARBi)}{n}$$

$$\alpha_{NLARB} = \sqrt{\frac{\sum_{i=1}^{n}(ARBi - \mu_{NLARB})^2}{n-1}}$$

where ARBi represents the ARB of the i-th non-leaking hotspot $\mu_{NLARB}$ represents the average ARB value of the non-leaking hotspot, and $\alpha_{NLARB}$ represents the standard deviation of ARB values for non-leaking hotspots.

Similarly, the mean and standard deviation of ARB values for leaking hotspots can be calculated as follows:

$$\mu_{LARB} = \frac{\sum_{i=1}^{n}(ARBi)}{n}$$

$$\alpha_{LARB} = \sqrt{\frac{\sum_{i=1}^{n}(ARBi - \mu_{LARB})^2}{n-1}}$$

where ARBi represents the ARB of the i-th leaking hotspot, $\mu_{LARB}$ represents the average ARB value of the leaking hotspot, and $\alpha_{LARB}$ represents the standard deviation of ARB values for leaking hotspots.

The ARB probability distributions for non-leaking (P3) and leaking (P4) hotspots with respect to a ARB threshold $ARB_0$ can be calculated in the following equations:

$$P_3(ARB \leq ARB_0) = \frac{1}{\sqrt{2\pi}\,\alpha_{NLARB}} \int_{-\infty}^{ARB_0} e^{-\frac{(ARB-\mu_{NLARB})^2}{2\alpha_{NLARB}^2}} dARB$$

$$P_4(ARB \geq ARB_0) = \frac{1}{\sqrt{2\pi}\,\alpha_{LARB}} \int_{ARB_0}^{\infty} e^{-\frac{(ARB-\mu_{LARB})^2}{2\alpha_{LARB}^2}} dARB$$

Figure 4B:
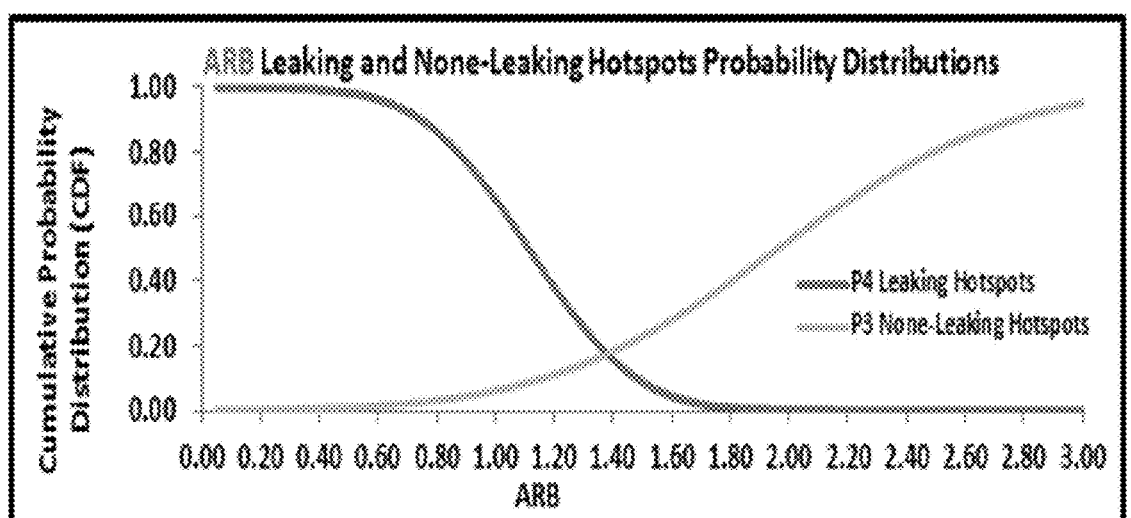
FIG. 4B is an example ARB probability distribution chart according to an implementation.

FIG. 4B is an example ARB probability distribution chart 420 according to an implementation. The example ARB probability distribution chart 420 includes ARB probability distribution curves for the leaking and non-leaking hotspots based on the above calculations. For example, as shown in FIG. 4B, 50% of the leaking hotspots have ARBs of about 2.1 or higher, while 50% of the non-leaking hotspots have ARBs of about 1.1 or higher.

Referring to FIG. 2, the mean and standard deviation of CR values for non-leaking hotspots can be calculated as follows:

$$\mu_{NLCR} = \frac{\sum_{i=1}^{n}(CRi)}{n}$$

$$\alpha_{NLCR} = \sqrt{\frac{\sum_{i=1}^{n}(CRi - \mu_{NLCR})^2}{n-1}}$$

where CRi represents the CR of the i-th non-leaking hotspot, $\mu_{NLCR}$ represents the average CR value of the non-leaking hotspot, and $\alpha_{NLCR}$ represents the standard deviation of CR values for non-leaking hotspots.

The CR probability distribution for non-leaking (P5) hotspots can be calculated in the following equation:

$$P_5(CR) = \frac{1}{\sqrt{2\pi}\,\alpha_{NLCR}} \times e^{-\frac{(CR-\mu_{NLCR})^2}{2\alpha_{NLCR}^2}}$$

Figure 4C:
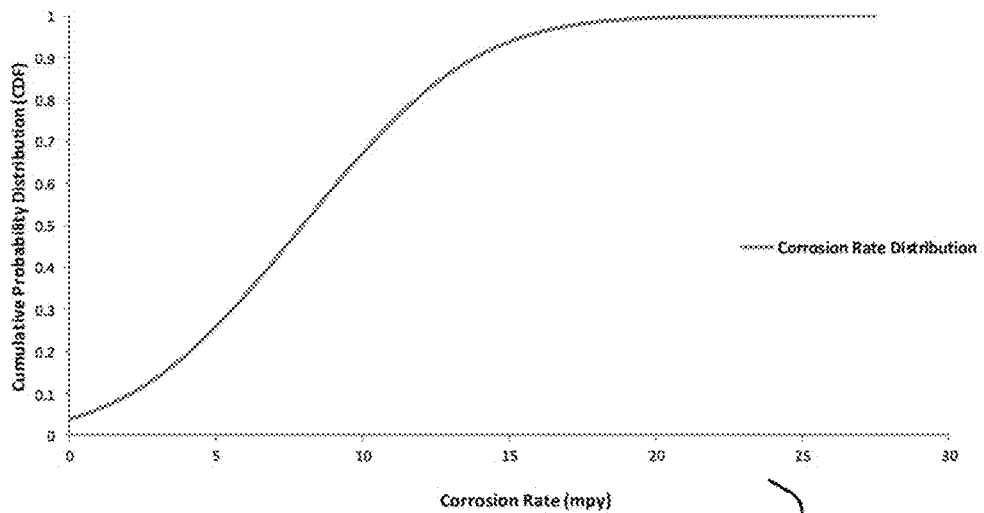
FIG. 4C is an example CR probability distribution chart according to an implementation.

FIG. 4C is an example CR probability distribution chart 430 according to an implementation. The example CR probability distribution chart 430 includes a CR probability distribution curve for the non-leaking hotspots based on the above calculations. For example, as shown in FIG. 4C, 50% of the non-leaking hotspots have CRs at about 7.5 mpy or higher.

Referring to FIG. 2, the mean and standard deviation of EL values for non-leaking hotspots can be calculated as follows:

$$\mu_{NLEL} = \frac{\sum_{i=1}^{n}(EL)i}{n}$$

$$\alpha_{NLEL} = \sqrt{\frac{\sum_{i=1}^{n}(ELi - \mu_{NLEL})^2}{n-1}}$$

where ELi represents the EL of the i-th non-leaking hotspot, $\mu_{NLEL}$ represents the average EL value of the non-leaking hotspot, and $\alpha_{NLEL}$ represents the standard deviation of EL values for non-leaking hotspots.

The EL probability distribution for non-leaking (P6) hotspots can be calculated in the following equation:

$$P_6(EL \leq EL_0) = \int_{-\infty}^{EL_0} \frac{1}{\sqrt{2\pi}\,\alpha_{NLEL}} e^{-\frac{(EL-\mu_{NLEL})^2}{2\alpha_{NLEL}^2}}$$

Figure 4D:
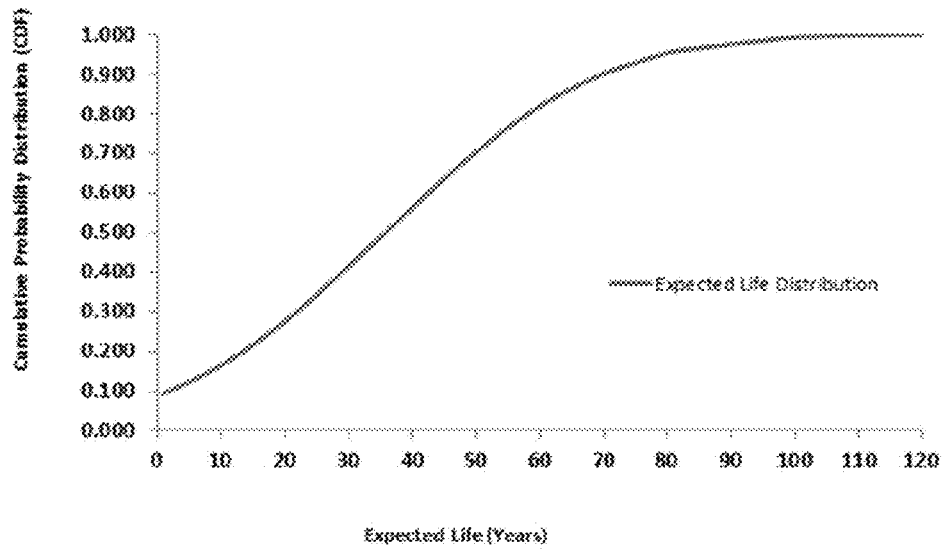
FIG. 4D is an example EL probability distribution chart according to an implementation.

FIG. 4D is an example EL probability distribution chart 440 according to an implementation. The example EL probability distribution chart 440 includes an EL probability distribution curve for the non-leaking hotspots based on the above calculations. For example, as shown in FIG. 4D, 50% of the non-leaking hotspots have ELs of 40 years or higher.

Referring back to FIG. 2, from 206, method 200 proceeds to 208.

At 208, a corrosion severity classification matrix is generated. In some cases, the corrosion severity classification matrix can be generated using risk-based cutoffs for the metal loss, ARB, CR, EL values, or any combination thereof. The risk-based cutoffs can be determined based on a function of standard deviations and the averages of the metal loss, ARB, CR, or EL values. For example, the cutoffs can be set as multiples of the standard deviations from the averages. The corrosion severity classification matrix can include a plurality of corrosion severity classes, each corresponding to a risk-based cutoff value.

FIG. 5A illustrates an example corrosion severity classification definition table 510 according to an implementation. The corrosion severity classification definition table 510 defines corrosion severity classes 0-3, where class 0 represents the class with most severe loss. As illustrated, cutoffs of the metal loss, ARB, CR, and EL values for each of the corrosion severity classes 0-3 are listed in the corrosion severity classification definition table 510. For example, $X_{ML0}$, $X_{ML1}$, and $X_{ML2}$ are cutoffs for the metal loss values. $X_{ML0}$ is set to the larger value of $(\mu_{LML} - \alpha_{LML})$ and $(\mu_{NLML} + \alpha_{NLML})$; $X_{ML1}$ is set to $X_{ML0} - \alpha_{NLML}$; $X_{ML2}$ is set to $X_{ML1} - \alpha_{NLML}$. For class 3, the average metal loss is less than $X_{ML2}$; for class 2, the average metal loss is between $X_{ML2}$ and $X_{ML1}$; for class 1, the average metal loss is between $X_{ML1}$ and $X_{ML0}$; and for class 0, the average metal loss is greater or equal to $X_{ML0}$. Cutoffs for ARB, CR, and EL can similarly be defined for each corrosion severity class.

FIG. 5B illustrates an example corrosion severity classification matrix 520 according to an implementation. The corrosion severity classification matrix 520 includes the numerical values of cutoffs for each class. The corrosion severity classification matrix 520 is generated based on the definitions listed in the corrosion severity classification definition table 510 and the numerical values of average metal loss, ARB, CR, and EL of more than 100 wells.

In some cases, each class is associated with one or more remedial measures or actions. This approach may alert the service companies about the different risk levels for each hotspot and, therefore, provision different actions. For example, each class can be associated with an inspection frequency. A more severe class may be associated with a higher inspection frequency. In some cases, the frequency can be calculated as a weighted average of the expected life values fallen within each class interval according to the severity classification matrix. A safety factor can also be included in the frequency calculation to account for the uncertainty of extrapolating the metal loss growth. This safety factor correlates with the variation of corrosion rate values. The following equation represents an example calculation of the safety factor as a function of the ratio between the lowest and the highest expected corrosion rates, respectively:

$$SF = \frac{CR_{z=-1}}{CR_{z=+1}}$$

where SF represents a dimensionless risk-based safety factor, $CR_{z=-1}$ represents the CR value one standard deviation less than the average value, and $CR_{z=+1}$ represents the CR value one standard deviation more than the average value. $CR_{z=-1}$ and $CR_{z=+1}$ are dependent on both the average and standard deviation of the corrosion rate data. Therefore, the safety factor is dynamic and can be updated when more corrosion rate data is collected. The following equation represents an example calculated of the corrosion logging frequency for each severity class:

$$Freq_i = SF \cdot \frac{\int_{ti}^{ti+1} f(t) t \, dt}{\int_{ti}^{ti+1} f(t) \, dt}$$

where, $Freq_i$ represents the corrosion logging frequency of the i-th class, $f(t)$ represents the probability density function of the EL values, and t represents the EL. As illustrated, the corrosion severity classification matrix 520 includes an inspection frequency of 2, 4, and 8 years for class 1, 2, and 3, respectively. The corrosion severity classification matrix 520 also indicates that class 0 has a high risk to develop a leak. By setting the remedial action for each class, the service company can determine the remedial action for each hotspot based on the classification of the hotspot and take the predefined remedial action accordingly.

Referring back to FIG. 2, from 208, method 200 proceeds to 210.

At 210, hotspots are grouped into the plurality of corrosion severity classes based on the corrosion severity classification matrix. In some cases, the grouping is based on the cutoffs defined in the matrix and the metal loss, ARB, CR, EL, or any combination thereof. For example, if a hotspot has an average metal loss between $X_{ML1}$ and $X_{ML0}$, an ARB between $X_{ARB1}$ and $X_{ARB0}$, an CR greater or equal to $X_{CR1}$, and an EL grater or equal to $X_{EL1}$, the hotspot can be grouped into class 1. In some cases, different parameters, e.g., the metal loss, ARB, CR, EL, of a hotspot may fall into ranges of different corrosion classes according to the corrosion severity classification matrix. In these or other cases, the hotspot may be classified based on the most severe class. For example, the average metal loss of a hotspot may be between $X_{ML1}$ and $X_{ML0}$, which may be the range for corrosion class 1, while the ARB of the hotspot may be between $X_{ARB2}$ and $X_{ARB1}$, which may be the range for corrosion class 2. In this example, the hotspot may be grouped into corrosion class 1, which is more severe than class 2.

The casing leaking prediction approach discussed is data driven and dynamic. For example, any combination of the steps discussed above can be the repeated when additional raw EM corrosion data is obtained. In one example, when additional raw corrosion data for one well is obtained, the metal loss, ARB, CR, and EL for the well can be calculated. A determination can be made on whether the well is leaking or not leaking. If the well is leaking, then the mean and average of the metal loss, ARB, CR, and EL of leaking hotspots can be updated to include the values of the well. The probability distribution curves for the leaking hotspots can also be re-generated accordingly. Similarly, if the well is not leaking, then the mean and average of the metal loss, ARB, CR, and EL of non-leaking hotspots can be updated to include the values of the well. The probability distribution curves for the non-leaking hotspots can also be re-generated accordingly, and accordingly, the corrosion severity classification matrix can also be updated. In some cases, the logging frequencies for different classes can also be re-calculated to incorporate the additional raw EM corrosion data.

Figure 3:
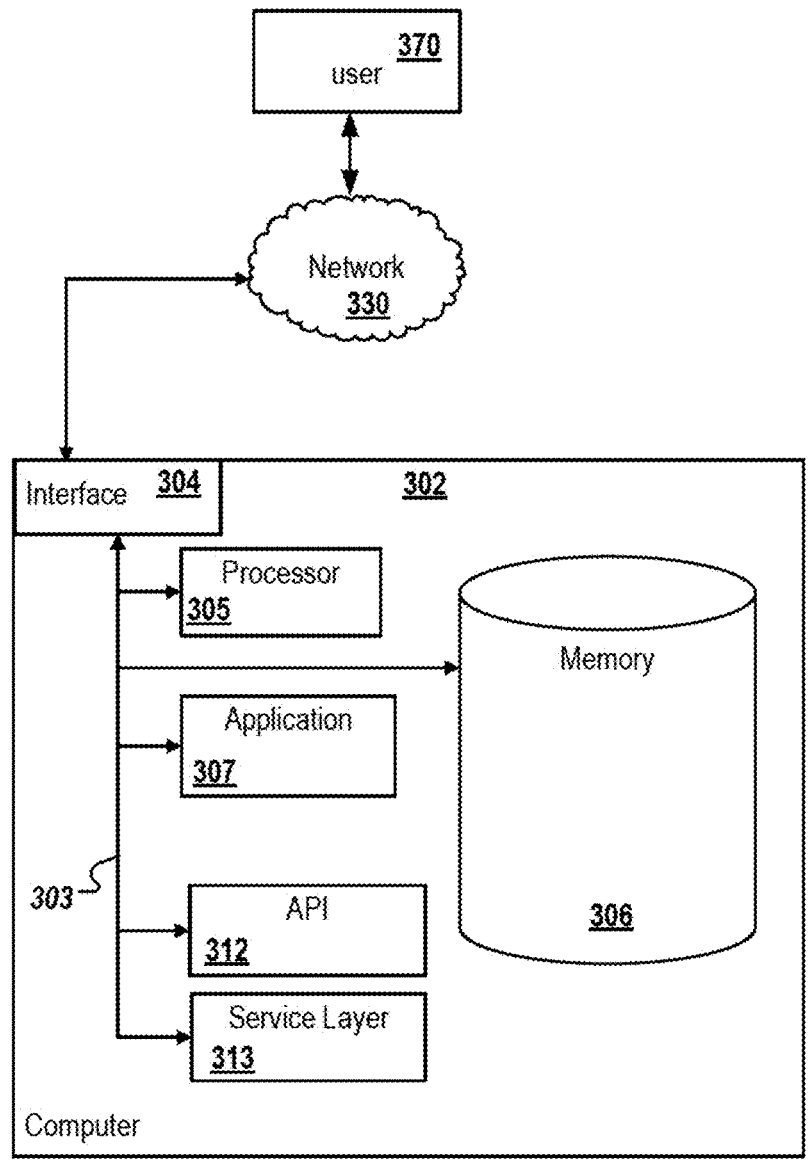
FIG. 3 is a high-level architecture block diagram of a casing leak prediction data processing system according to an implementation.

FIG. 3 is a high-level architecture block diagram of a casing leak prediction data processing system 300 according to an implementation. At a high level, the illustrated system 300 includes a user 370 that is communicably coupled with a casing leak prediction data processing computer 302 through a network 330. The described illustration is only one possible implementation of the described subject matter and is not intended to limit the disclosure to the single described implementation. Those of ordinary skill in the art will appreciate the fact that the described components can be connected, combined, and/or used in alternative ways consistent with this disclosure.

The user 370 represents a person, an application, set of applications, software, software modules, hardware, or combination thereof that can be used to predict casing leaks. For example, the user 370 can be a service personnel in a service company that is responsible for well maintenance.

The network 330 facilitates communications between the components of the system 300 (e.g., between the user 370 and the casing leak prediction data processing computer 302). In some cases, the user 370 can access the casing leak prediction data processing computer 302 from a remote network. In these or other cases, the network 330 can be a wireless or a wireline network. In some cases, the user 370 can access the casing leak prediction data processing computer 302 locally. In these or other cases, the network 330 can also be a memory pipe, a hardware connection, or any internal or external communication paths between the components.

The casing leak prediction data processing computer 302 includes a computing system configured to predict casing leaks. In some cases, the algorithm of the casing leak prediction process can be implemented in an executable computing code, e.g., C/C++ executable codes. Alternatively or in combination, the algorithm of the casing leak prediction process can be implemented in an application program, e.g., EXCEL. In some cases, the casing leak prediction data processing computer 302 can include a standalone Linux system that runs batch applications. In some cases, the casing leak prediction processing computer 302 can include mobile or personal computers that run the application program.

The computer 302 may comprise a computer that includes an input device, such as a keypad, keyboard, touch screen, microphone, speech recognition device, other device that can accept user information, and/or an output device that conveys information associated with the operation of the computer 302, including digital data, visual and/or audio information, or a GUI.

The computer 302 can serve as a client, network component, a server, a database or other persistency, and/or any other component of the system 300. In some implementations, one or more components of the computer 302 may be configured to operate within a cloud-computing-based environment.

At a high level, the computer 302 is an electronic computing device operable to receive, transmit, process, store, or manage data and information associated with the system 300. According to some implementations, the computer 302 may also include or be communicably coupled with an application server, e-mail server, web server, caching server, streaming data server, business intelligence (BI) server, and/or other server.

The computer 302 can receive requests over network 330 from a client application (e.g., executing on another computer 302) and respond to the received requests by processing the said requests in an appropriate software application. In addition, requests may also be sent to the computer 302 from internal users (e.g., from a command console or by another appropriate access method), external or third parties, other automated applications, as well as any other appropriate entities, individuals, systems, or computers.

Each of the components of the computer 302 can communicate using a system bus 503. In some implementations, any and/or all the components of the computer 302, both hardware and/or software, may interface with each other and/or the interface 304 over the system bus 303 using an application programming interface (API) 312 and/or a service layer 313. The API 312 may include specifications for routines, data structures, and object classes. The API 312 may be either computer language-independent or -dependent and refer to a complete interface, a single function, or even a set of APIs. The service layer 313 provides software services to the computer 302 and/or the system 300. The functionality of the computer 302 may be accessible for all service consumers using this service layer. Software services, such as those provided by the service layer 313, provide reusable, defined business functionalities through a defined interface. For example, the interface may be software written in JAVA, C++, or other suitable language providing data in Extensible Markup Language (XML) format or other suitable format. While illustrated as an integrated component of the computer 302, alternative implementations may illustrate the API 312 and/or the service layer 313 as stand-alone components in relation to other components of the computer 302 and/or system 300. Moreover, any or all parts of the API 312 and/or the service layer 313 may be implemented as child or sub-modules of another software module, enterprise application, or hardware module without departing from the scope of this disclosure.

The computer 302 includes an interface 304. Although illustrated as a single interface 304 in FIG. 3, two or more interfaces 304 may be used according to particular needs, desires, or particular implementations of the computer 302 and/or system 300. The interface 304 is used by the computer 302 for communicating with other systems in a distributed environment—including within the system 300—connected to the network 330 (whether illustrated or not). Generally, the interface 304 comprises logic encoded in software and/or hardware in a suitable combination and operable to communicate with the network 330. More specifically, the interface 304 may comprise software supporting one or more communication protocols associated with communications such that the network 330 or interface's hardware is operable to communicate physical signals within and outside of the illustrated system 300.

The computer 302 includes a processor 305. Although illustrated as a single processor 305 in FIG. 3, two or more processors may be used according to particular needs, desires, or particular implementations of the computer 302 and/or the system 300. Generally, the processor 305 executes instructions and manipulates data to perform the operations of the computer 302. Specifically, the processor 305 executes the functionality required for predicting casing leaks.

The computer 302 also includes a memory 306 that holds data for the computer 302 and/or other components of the system 300. Although illustrated as a single memory 306 in FIG. 3, two or more memories may be used according to particular needs, desires, or particular implementations of the computer 302 and/or the system 300. While memory 306 is illustrated as an integral component of the computer 302, in alternative implementations, memory 306 can be external to the computer 302 and/or the system 300.

The application 307 is an algorithmic software engine providing functionality according to particular needs, desires, or particular implementations of the computer 302 and/or the system 300, particularly with respect to functionality required for predicting casing leaks. For example, application 307 can serve as one or more components/applications described in FIGS. 1-2 and 4-6. Further, although illustrated as a single application 307, the application 307 may be implemented as multiple applications 307 on the computer 302. In addition, although illustrated as integral to the computer 302, in alternative implementations, the application 307 can be external to the computer 302 and/or the system 300.

There may be any number of computers 302 associated with, or external to, the system 300 and communicating over network 330. Further, the terms "client," "user," and other appropriate terminology may be used interchangeably as appropriate without departing from the scope of this disclosure. Moreover, this disclosure contemplates that many users may use one computer 302, or that one user may use multiple computers 302.

Implementations of the subject matter and the functional operations described in this specification can be implemented in digital electronic circuitry, in tangibly embodied computer software or firmware, in computer hardware, including the structures disclosed in this specification and their structural equivalents, or in combinations of one or more of them. Implementations of the subject matter described in this specification can be implemented as one or more computer programs, i.e., one or more modules of computer program instructions encoded on a tangible, non-transitory computer-storage medium for execution by, or to control the operation of, data processing apparatus. Alternatively or in addition, the program instructions can be encoded on an artificially generated propagated signal, e.g., a machine-generated electrical, optical, or electromagnetic signal that is generated to encode information for transmission to suitable receiver apparatus for execution by a data processing apparatus. The computer-storage medium can be a machine-readable storage device, a machine-readable storage substrate, a random or serial access memory device, or a combination of one or more of them.

The terms "data processing apparatus," "computer," or "electronic computer device" (or equivalent as understood by one of ordinary skill in the art) refer to data processing hardware and encompass all kinds of apparatus, devices, and machines for processing data, including by way of example, a programmable processor, a computer, or multiple processors or computers. The apparatus can also be or further include special purpose logic circuitry, e.g., a central processing unit (CPU), an FPGA (field programmable gate array), or an ASIC (application-specific integrated circuit). In some implementations, the data processing apparatus and/or special purpose logic circuitry may be hardware-based and/or software-based. The apparatus can optionally include code that creates an execution environment for computer programs, e.g., code that constitutes processor firmware, a protocol stack, a database management system, an operating system, or a combination of one or more of them. The present disclosure contemplates the use of data processing apparatuses with or without conventional operating systems, for example LINUX, UNIX, WINDOWS, MAC OS, ANDROID, IOS or any other suitable conventional operating system.

A computer program, which may also be referred to or described as a program, software, a software application, a module, a software module, a script, or code, can be written in any form of programming language, including compiled or interpreted languages, or declarative or procedural languages, and it can be deployed in any form, including as a stand-alone program or as a module, component, subroutine, or other unit suitable for use in a computing environment. A computer program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub-programs, or portions of code. A computer program can be deployed to be executed on one computer or on multiple computers that are located at one site or distributed across multiple sites and interconnected by a communication network. While portions of the programs illustrated in the various figures are shown as individual modules that implement the various features and functionality through various objects, methods, or other processes, the programs may instead include a number of sub-modules, third-party services, components, libraries, and such, as appropriate. Conversely, the features and functionality of various components can be combined into single components as appropriate.

The processes and logic flows described in this specification can be performed by one or more programmable computers executing one or more computer programs to perform functions by operating on input data and generating output. The processes and logic flows can also be performed by, and apparatus can also be implemented as, special purpose logic circuitry, e.g., a CPU, an FPGA, or an ASIC.

Computers suitable for the execution of a computer program can be based on general or special purpose microprocessors, both, or any other kind of CPU. Generally, a CPU will receive instructions and data from a read-only memory (ROM) or a random access memory (RAM) or both. The essential elements of a computer are a CPU for performing or executing instructions and one or more memory devices for storing instructions and data. Generally, a computer will also include, or be operatively coupled to, receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a global positioning system (GPS) receiver, or a portable storage device, e.g., a universal serial bus (USB) flash drive, to name just a few.

Computer-readable media (transitory or non-transitory, as appropriate) suitable for storing computer program instructions and data include all forms of non-volatile memory, media and memory devices, including by way of example semiconductor memory devices, e.g., erasable programmable read-only memory (EPROM), electrically erasable programmable read-only memory (EEPROM), and flash memory devices; magnetic disks, e.g., internal hard disks or removable disks; magneto-optical disks; and CD-ROM, DVD+/−R, DVD-RAM, and DVD-ROM disks. The memory may store various objects or data, including caches, classes, frameworks, applications, backup data, jobs, web pages, web page templates, database tables, repositories storing business and/or dynamic information, and any other appropriate information including any parameters, variables, algorithms, instructions, rules, constraints, or references thereto. Additionally, the memory may include any other appropriate data, such as logs, policies, security or access data, reporting files, as well as others. The processor and the memory can be supplemented by, or incorporated in, special purpose logic circuitry.

To provide for interaction with a user, implementations of the subject matter described in this specification can be implemented on a computer having a display device, e.g., a CRT (cathode ray tube), LCD (liquid crystal display), LED (Light Emitting Diode), or plasma monitor, for displaying information to the user and a keyboard and a pointing device, e.g., a mouse, trackball, or trackpad by which the user can provide input to the computer. Input may also be provided to the computer using a touchscreen, such as a tablet computer surface with pressure sensitivity, a multi-touch screen using capacitive or electric sensing, or other type of touchscreen. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

The term "graphical user interface," or "GUI," may be used in the singular or the plural to describe one or more graphical user interfaces and each of the displays of a particular graphical user interface. Therefore, a GUI may represent any graphical user interface, including but not limited to, a web browser, a touch screen, or a command line interface (CLI) that processes information and efficiently presents the information results to the user. In general, a GUI may include a plurality of user interface (UI) elements, some or all associated with a web browser, such as interactive fields, pull-down lists, and buttons operable by the business suite user. These and other UI elements may be related to or represent the functions of the web browser.

Implementations of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described in this specification, or any combination of one or more such back-end, middleware, or front-end components. The components of the system can be interconnected by any form or medium of wireline and/or wireless digital data communication, e.g., a communication network. Examples of communication networks include a local area network (LAN), a radio access network (RAN), a metropolitan area network (MAN), a wide area network (WAN), Worldwide Interoperability for Microwave Access (WIMAX), a wireless local area network (WLAN) using, for example, 802.11 a/b/g/n and/or 802.20, all or a portion of the Internet, and/or any other communication system or systems at one or more locations. The network may communicate with, for example, Internet Protocol (IP) packets, Frame Relay frames, Asynchronous Transfer Mode (ATM) cells, voice, video, data, and/or other suitable information between network addresses.

The computing system can include clients and servers. A client and server are generally remote from each other and typically interact through a communication network. The relationship of client and server arises by virtue of computer programs running on the respective computers and having a client-server relationship to each other.

In some implementations, any or all of the components of the computing system, both hardware and/or software, may interface with each other and/or the interface using an application programming interface (API) and/or a service layer. The API may include specifications for routines, data structures, and object classes. The API may be either computer language independent or dependent and refer to a complete interface, a single function, or even a set of APIs. The service layer provides software services to the computing system. The functionality of the various components of the computing system may be accessible for all service consumers via this service layer. Software services provide reusable, defined business functionalities through a defined interface. For example, the interface may be software written in JAVA, C++, or other suitable language providing data in extensible markup language (XML) format or other suitable format. The API and/or service layer may be an integral and/or a stand-alone component in relation to other components of the computing system. Moreover, any or all parts of the service layer may be implemented as child or sub-modules of another software module, enterprise application, or hardware module without departing from the scope of this disclosure.

While this specification contains many specific implementation details, these should not be construed as limitations on the scope of any invention or on the scope of what may be claimed, but rather as descriptions of features that may be specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Particular implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results. In certain circumstances, multitasking and parallel processing may be advantageous.

Moreover, the separation and/or integration of various system modules and components in the implementations described above should not be understood as requiring such separation and/or integration in all implementations, and it should be understood that the described program components and systems can generally be integrated together in a single software product or packaged into multiple software products.

Accordingly, the above description of example implementations does not define or constrain this disclosure. Other changes, substitutions, and alterations are also possible without departing from the spirit and scope of this disclosure.

What is claimed is:

1. A system for predicting downhole casing leaks of hotspots, comprising:
    a memory; and at least one hardware processor interoperably coupled with the memory and configured to:

obtain, from corrosion logs generated by an electromagnetic (EM) logging tool, raw EM corrosion data for a hotspot, wherein the raw EM corrosion data includes a metal thickness loss value for the hotspot;

determine a corrosion parameter based on the raw EM corrosion data, wherein the corrosion parameter includes a corrosion rate that is calculated based on an original thickness value, a remaining thickness value, and a number of years;

generate a probability distribution curve for the corrosion parameter;

generate a corrosion severity classification matrix based on the probability distribution curve, wherein the corrosion severity classification matrix includes a plurality of corrosion severity classes and cutoff values for each of the plurality of corrosion severity classes;

assign the hotspot into one of the plurality of corrosion severity classes based on a comparison of the cutoff values for the plurality of corrosion severity classes in the corrosion severity classification matrix and the corrosion parameter of the hotspot; and generate a service alert for the hotspot based on the assigned corrosion severity class.

2. The system of claim 1, wherein the generation of the probability distribution curve comprises:

determining whether the hotspot is a leaking hotspot or a non-leaking hotspot;

if the hotspot is a leaking hotspot, generating a probability distribution curve for the corrosion parameter based on corrosion parameters for leaking hotspots; and if the hotspot is a non-leaking hotspot, generating a probability distribution curve for the corrosion parameter based on corrosion parameters for non-leaking hotspots.

3. The system of claim 1, wherein the raw EM corrosion data includes metal loss values for a plurality of strings, and the corrosion parameter includes an average remaining barrier that is calculated based on a nominal thickness value for each of the plurality of strings, and a thickness loss value for each of the plurality of strings.

4. The system of claim 1, wherein the generation of the probability distribution curve for the corrosion parameter comprises:

calculating a mean value and a standard deviation value of the corrosion parameter for leaking hotspots;

calculating a mean value and a standard deviation value of the corrosion parameter for non-leaking hotspots;

generating a probability distribution function of the leaking hotspots based on the mean value and the standard deviation value of the corrosion parameter for leaking hotspots; and generating a probability distribution function of the non-leaking hotspots based on the mean value and the standard deviation value of the corrosion parameter for non-leaking hotspots.

5. The system of claim 1, wherein the cutoff values for each of the plurality of corrosion severity classes is determined based on a mean value of the corrosion parameter for leaking hotspots, a standard deviation value of the corrosion parameter for leaking hotspots, a mean value of the corrosion parameter for non-leaking hotspots, and a standard deviation value of the corrosion parameter for non-leaking hotspots.

6. The system of claim 1, wherein each of the plurality of corrosion severity classes is associated with a logging frequency for the respective corrosion severity class.

* * * * *